US012702661B2

(12) United States Patent
Garibaldi

(10) Patent No.: US 12,702,661 B2
(45) Date of Patent: Aug. 11, 2026

(54) METHODS OF PREPARING MATRIX PELLET COMPOSITIONS

(71) Applicant: Noema Pharma AG, Basel (CH)

(72) Inventor: George Garibaldi, Basel (CH)

(73) Assignee: Noema Pharma AG, Basel (CH)

(*) Notice: Subject to any disclaimer, the term of this patent is extended or adjusted under 35 U.S.C. 154(b) by 0 days.

(21) Appl. No.: 18/641,640

(22) Filed: Apr. 22, 2024

(65) Prior Publication Data

US 2025/0099445 A1 Mar. 27, 2025

Related U.S. Application Data

(63) Continuation of application No. 18/315,723, filed on May 11, 2023, now Pat. No. 11,998,535, which is a continuation of application No. 18/061,239, filed on Dec. 2, 2022, now Pat. No. 11,684,613, which is a continuation of application No. PCT/EP2021/065075, filed on Jun. 4, 2021.

(60) Provisional application No. 63/035,313, filed on Jun. 5, 2020.

(51) Int. Cl.
*A61K 31/4439* (2006.01)
*A61P 35/00* (2006.01)

(52) U.S. Cl.
CPC .......... *A61K 31/4439* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 4,508,560 | A | 4/1985 | Brunner et al. | |
| 7,332,510 | B2 | 2/2008 | Buettelmann et al. | |
| 8,063,076 | B2 * | 11/2011 | Cleary | A61P 25/04 514/341 |
| 11,684,613 | B2 * | 6/2023 | Garibaldi | A61P 35/00 514/341 |
| 11,998,535 | B2 * | 6/2024 | Garibaldi | A61P 25/00 |
| 2006/0030559 | A1 | 2/2006 | Buettelmann et al. | |
| 2008/0312288 | A1 | 12/2008 | Cleary et al. | |
| 2009/0239919 | A1 | 9/2009 | Wood et al. | |

FOREIGN PATENT DOCUMENTS

| | | | | |
|---|---|---|---|---|
| WO | 03024453 | A1 | 3/2003 | |
| WO | 2004080998 | A1 | 9/2004 | |
| WO | WO-2004108701 | A1 | 12/2004 | |
| WO | 2005118568 | A1 | 12/2005 | |
| WO | WO-2008074697 | A1 | 6/2008 | |
| WO | WO-2011035209 | A1 | 3/2011 | |
| WO | WO2012/019990 | A2 * | 2/2012 | A61K 9/16 |
| WO | WO-2012019989 | A2 | 2/2012 | |
| WO | 2013028590 | A1 | 2/2013 | |
| WO | WO-2022/023519 | A1 | 2/2022 | |
| WO | 2023279193 | A2 | 1/2023 | |
| WO | 2023244530 | A1 | 12/2023 | |
| WO | 2024054811 | A1 | 3/2024 | |
| WO | 2024088712 | A1 | 5/2024 | |
| WO | WO-2024/163890 | A1 | 8/2024 | |
| WO | 2024189127 | A1 | 9/2024 | |

OTHER PUBLICATIONS

Singh et al., Journal of Young Pharmacists (2012), 4(3), pp. 146-156.*

Cao et al., "Preparation of Sotalol Hydrochloride Sustained-Release Matrix Pellets by Extrusion-Spheronization Method" Journal of Pharmaceutical Research vol. 32, No. 3, pp. 162-164, (Mar. 15, 2013).

Elkommos et al., "Current and future pharmacotherapy options for drug-resistant epilepsy" Expert Opinion on Pharmacotherapy, vol. 23, Issue 18 (2022).

International Search Report and Written Opinion mailed May 15, 2024, for International Application No. PCT/US2024/014248 filed Feb. 2, 2024. (16 pages).

Jong, Y.-J. I., S. K. Harmon and K. L. O'Malley (2019). "Location and Cell-Type-Specific Bias of Metabotropic Glutamate Receptor, mGlu5, Negative Allosteric Modulators." ACS Chemical Neuroscience 10(11): 4558-4570.

Quiroz et al., "Efficacy and Safety of Basimglurant as Adjunctive Therapy for Major Depression" JAMA Psychiatry, 73(7):675-684 (2016).

Silvinato et al., "Use of cannabidiol in the treatment of epilepsy: Lennox-Gastaut syndrome, Dravet syndrome, and tuberous sclerosis complex" Rev Assoc Med Bras, 68(10):1345-1357 (2022).

Vincent, K., S. F. Wang, A. Laferrière, N. Kumar and T. J. Coderre (2017). "Spinal intracellular metabotropic glutamate receptor 5 (mGluR5) contributes to pain and c-fos expression in a rat model of inflammatory pain." Pain 158(4): 705-716.

Youssef et al., "Effect of the mGluR5-NAM Basimglurant on Behavior in Adolescents and Adults with Fragile X Syndrome in a Randomized, Double-Blind, Placebo-Controlled Trial: FragXis Phase 2 Results" Neuropsychopharmacology, 43, 503-512 (2018).

Chen, HI et al., "The Measurement of Pain in Patients With Trigeminal Neuralgia," Clinical Neurosurgery Proceedings, 2010, vol. 0, pp. 1-7, The Congress of Neurological Surgeons.

Kelly, E et al. "mGluR5 modulation of behavioural and epileptic phenotypes in a mouse model of tuberous sclerosis complex" Neuropsychopharmacology, vol. 43, No. 6, Dec. 5, 2017, pp. 1457-1465, XP036968571, Springer Nature, New York, NY, US (ISSN: 0893-133X, DOI: 10.1038/npp. 2017.295).

(Continued)

*Primary Examiner* — Brian J Davis

(74) *Attorney, Agent, or Firm* — Goodwin Procter LLP

(57) ABSTRACT

Provided herein are methods of treating tuberous sclerosis complex in a subject in need thereof by administering to the subject compositions comprising an mGlu5 negative allosteric modulator (NAM), having the structure of Formula I:

(I)

13 Claims, 2 Drawing Sheets

(56) References Cited

OTHER PUBLICATIONS

Nickols, HH et al. "Development of allosteric modulators of GPCRs for treatment of CNS disorders" Neurobiology of Disease, vol. 61, Sep. 27, 2013, pp. 55-71, Elsevier, Philadelphia, PA, US (ISSN: 0969-9961, DOI: 10.1016/J.NBD.2013.09.013).
International Search Report and Written Opinion mailed Nov. 22, 2021, for International Application No. PCT/EP2021/071376 filed Jul. 30, 2021. (12 pages).
International Search Report and Written Opinion mailed Sep. 7, 2021, for International Application No. PCT/EP2021/065075 filed Jun. 4, 2021. (18 pages).
Mcginity, JW et al. "Oral controlled-release polymeric drug delivery systems" Engineering Polymer Systems for Improved Drug Delivery, Dec. 27, 2013, John Wiley & Sons, Hoboken, NJ, US, (ISBN: 978-1-118-09847-9, pp. 283-318, DOI: 10.1002/9781118747896.ch9, URL: https://onlinelibrary.wiley.com/doi/pdfdirect/10.1002/9781118747896.ch9>.
Jaeschke, G et al., "Metabotropic Glutamate Receptor 5 Negative Allosteric Modulators: Discovery of 2-Chloro-4-[1-(4-fluorophenyl)-2,5-dimethyl-1H-imidazol-4-ylethynyl]pyridine (Basimglurant, RO4917523), a Promising Novel Medicine for Psychiatric Diseases," Journal of Medicinal Chemistry (2015), vol. 58, No. 3, pp. 1358-1371.
Perez, C et al., "Patient-reported outcomes in subjects with painful trigeminal neuralgia receiving pregabalin: evidence from medical practice in primary care settings," Cephalagia, 2009, vol. 29, pp. 781-790, Blackwell Publishing Ltd (doi: :10.1111/j.1468-2982.2008.01792.x).
Fowler, S et al. "Low potential of basimglurant to be involved in drug-drug interactions: influence of non-Michaelis-Menten P450 kinetics on fraction metabolised" Journal of Pharmacology and Experimental Therapeutics, vol. 360, No. 1, Dec. 15, 2016, pp. 164-173, American Society for Pharmacology and Experimental Therapeutics, Rockville, MD, US (ISSN: 0022-3565, DOI: 10.1124/jpet.116.237214).
Isherwood, SN et al. "Bidirectional variation in glutamate efflux in the medial prefrontal cortex induced by selective positive and negative allosteric mGluR5 modulators" Journal of Neurochemistry, vol. 145, No. 2, Feb. 12, 2018, pp. 111-124, John Wiley & Sons, London, GB (ISSN: 0022-3042, DOI: 10.1111/jnc.14290).
Abushik, P. A. et al., The role of NMDA and mGluR5 receptors in calcium mobilization and neurotoxicity of homocysteine in trigeminal and cortical neurons and glial cells, Journal of Neurochemistry, vol. 129, pp. 264-274, 2014.
Bowles et al., Phase I Study of Oral Rigosertib (ON 01910.Na), a Dual Inhibitor of the PI3K and Plk1 Pathways, in Adult Patients with Advanced Solid Malignancies, Cancer Thereapy, vol. 20, Issue 6, Mar. 2014.
Jones, R., et al., Application of Empirical Scalars To Enable Early Prediction of Human Hepatic Clearance Using In Vitro-In Vivo Extrapolation in Drug Discovery: An Evaluation of 173 Drugs, Drug Metabolism & Disposition, 50(8): 1053-1063 (2022).
Miljanovic, N., et al., Proteomic signature of the Dravet syndrome in the genetic Scn1a-A1783V mouse model, Neurobiology of Disease, 157: 1-17 (2021).
Noema Pharma AG, Clinical Study Report Synopsis, 7 pages, Sep. 2025.
Noema Pharma AG, Clinical Trial Results, Basimglurant, 6 pages, 2024.
Olnes et al., Directed therapy for patients with myelodysplastic syndromes (MDS) by suppression of cyclin D1 with ON 01910.Na, Leukemia Research, vol. 36, Issue 8, pp. 982-989, Aug. 2012.
Song J. et al., Signal Transduction Mechanisms Underlying Group I Mglur-Mediated Increase in Frequency and Amplitude of Spontaneous EPSCs in the Spinal Trigeminal Subnucleus Oralis of the Rat, Sage Journals, vol. 5, 15 pages, Jan. 2009.
Watkins, LV., et al., Pharmacological management of fragile X syndrome: a systematic review and narrative summary of the current evidence, Expert Opinion on Pharmacotherapy , 25(3): 301-313 (2024).
Witkin, JM., et al., Clinical investigations of compounds targeting metabotropic glutamate receptors, Pharmacology, Biochemistry and Behavior (2022) , vol. 219, 173446 (17 pages).
Wu, J., et al., Efficacy and safety of adjunctive antiseizure medications for dravet syndrome: A systematic review and network meta-analysis Front. Pharmacol, vol. 13, 1-15 (2022).
Waung et al., Metabotropic glutamate receptor 5: a target for migraine therapy, Annals of Clinical and Translational Neurology, vol. 3, No. 8, pages, Jul. 2016.
Hoffman et al., Glutamate and its Receptors as Therapeutic Targets for Migraine, Neurotherapeutics, vol. 15, No. 2, pp. 361-370, Mar. 2018.
Rehana Begum, A study on Different Pellet Formation Techniques and its Evaluation Parameters—A Review, International Journal of Current Pharmaceutical Reasearch, vol. 11, No. 2, pp. 7-13, Mar. 2019.
Yan Yao-dong, Design and Development of Sustained-Release and Controlled-Release Formulations, China Medical Science Press, pp. 287-288, 2006.

* cited by examiner

METHODS OF PREPARING MATRIX PELLET COMPOSITIONS

CROSS-REFERENCE TO RELATED APPLICATION

This application is a continuation of U.S. patent application Ser. No. 18/315,723, filed on May 11, 2023, which is a continuation of U.S. patent application Ser. No. 18/061,239, filed on Dec. 2, 2022, now U.S. Pat. No. 11,684,613, issued Jun. 27, 2023, which is a continuation of International Application Number PCT/EP2021/065075, filed on Jun. 4, 2021, which claims priority to U.S. Provisional Patent Application No. 63/035,313 filed on Jun. 5, 2020, the contents of each of which are incorporated herein by reference in its entirety.

FIELD

The present disclosure relates to the field of medicine and the treatment of medical conditions associated with tuberous sclerosis complex. More specifically, the present disclosure relates to use of compositions comprising 2-chloro-4-[1-(4-fluorophenyl)-2,5-dimethyl-1H-imidazol-4-ylethynyl]pyridine, or a pharmaceutically acceptable salt thereof, in the treatment or amelioration of medical conditions associated with tuberous sclerosis complex.

BACKGROUND

Tuberous sclerosis complex (TSC) is a genetic disorder characterized by the growth of numerous noncancerous tumors in many parts of the body such as the skin, brain, kidneys, and other organs. TSC can cause developmental issues and in some cases lead to significant health problems. Typically, TSC results from mutations in the TSC1 or TSC2 gene, which codes for the proteins hamartin and tuberin, respectively, with TSC2 mutations accounting for the majority and tending to cause more severe symptoms.

There is currently no cure for TSC. While medications such as antiepileptics can help treat certain types of disorders associated with TSC (e.g., seizures), some of these medications have significant side effects, thereby limiting their medical use.

Therefore, there is an unmet medical need to develop new methods for treating TSC without significant side effects.

SUMMARY

In one aspect, provided herein are methods of treating medical conditions associated with tuberous sclerosis complex (TSC), comprising administering to a subject in need thereof a composition containing a therapeutically effective amount of a compound or a pharmaceutically acceptable salt thereof, wherein the compound is of Formula I:

(I)

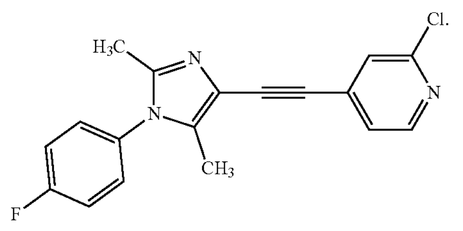

Cl.

In some embodiments, treating uses a composition comprising a crystalline anhydrate form (Form A) of a monosulfate salt of the compound of Formula I, wherein Form A has an X-ray powder diffraction (XRPD) pattern as substantially shown in FIG. 1. Specifically, Form A is characterized by the following X-ray powder diffraction peaks obtained with a $Cu_{K\alpha}$ radiation at 2θ (2 Theta): 9.8±0.2°, 13.4±0.2°, 14.2±0.2°, 18.1±0.2°, 18.9±0.2°, 19.6±0.2°, 22.6±0.2°, 22.9±0.2°, 25.7±0.2°, 27.1±0.2°, and 29.9±0.2°. The crystalline Form A typically has a $T_m$ of about 180-190° C. by differential scanning calorimetry (DSC) analysis.

In some embodiments, treating uses a composition comprising a crystalline monohydrate form (Form B) of a monosulfate salt of the compound of Formula I, wherein Form B has an XRPD pattern as substantially shown in FIG. 2. The crystalline Form B typically has a $T_m$ of about 60-70° C. by DSC analysis.

In some embodiments, treating uses a composition comprising a crystalline hemihydrate form (Form C) of a hemisulfate salt of the compound of Formula I, wherein Form C has an XRPD pattern as substantially shown in FIG. 3. The crystalline Form C typically has a $T_m$ of about 90-100° C. by DSC analysis.

In some embodiments, the composition used is a tablet formulation such as a modified release tablet formulation, or a matrix pellet formulation such as a modified release matrix pellet formulation, which can be encapsulated in a capsule, as defined herein.

In some embodiments, treating uses a composition comprising a pharmaceutically acceptable salt of the compound of Formula I, wherein said salt is 90% by weight or more (e.g., 95% by weight or more, or 99% by weight or more) in crystalline Form A based on the total weight of the salt present in the composition.

The present disclosure also includes a solid pharmaceutical composition comprising a solid form of a compound of Formula I:

(I)

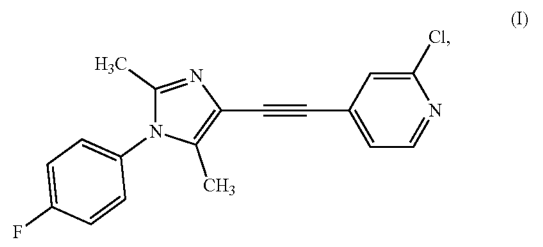 [SMILES: Cc1nc(C#Cc2ccnc(Cl)c2)c(C)n1-c1ccc(F)cc1]

Cl, wherein the solid form is a crystalline anhydrate form (Form A) of a monosulfate salt of the compound of Formula I, characterized by at least three peaks selected from the following XRPD peaks obtained with a $Cu_{K\alpha}$ radiation at 2θ (2 Theta): 9.8±0.2°, 13.4±0.2°, 14.2±0.2°, 18.1±0.2°, 18.9±0.2°, 19.6±0.2°, 22.6±0.2°, 22.9±0.2°, 25.7±0.2°, 27.1±0.2°, and 29.9±0.2°; and has a median particle size (Dv50) of less than or equal to about 100 μm, wherein the solid pharmaceutical composition is the form of a matrix pellet. In some embodiments, the solid form has a particle size of less than 47 μm (e.g., about 25 μm or less, or about 10 μm or less).

In some embodiments, the pharmaceutical composition comprises the Form A monosulfate salt characterized by the following XRPD peaks obtained with a $Cu_{K\alpha}$ radiation at 2θ (2 Theta): 9.8±0.2°, 13.4±0.2°, 14.2±0.2°, 18.1±0.2°, 18.9±0.2°, 19.6±0.2°, 22.6±0.2°, 22.9±0.2°, 25.7±0.2°, 27.1±0.2°, and 29.9±0.2°.

In some embodiments, the pharmaceutical composition comprises the Form A monosulfate salt characterized by an XRPD pattern as substantially shown in FIG. 1.

The present disclosure also includes a method of preparing a matrix pellet comprising a crystalline anhydrate form (Form A) of a monosulfate salt of a compound of Formula I:

(I)

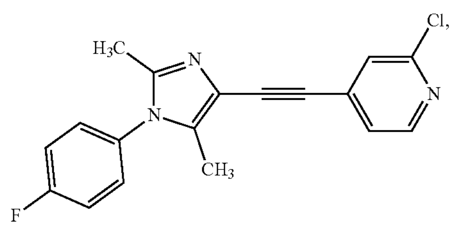

wherein the method comprises: granulating the Form A monosulfate salt and one or more polymers with purified water to form a mixture; extruding, spheronizing, drying, and sieving the mixture to afford a solid material; and blending the solid material with another pharmaceutical excipient to afford a matrix pellet.

In some embodiments, the method of preparation further comprises filling the matrix pellet into a capsule to form a matrix pellet capsule. In some embodiments, the one or more polymers are selected from the group consisting of a cellulose such as microcrystalline cellulose, methacrylic acid copolymer, and hypromellose. In some embodiments, the other pharmaceutical excipient is talc.

In another aspect, provided herein are methods of treating TSC, comprising administering to a subject in need thereof a composition containing a therapeutically effective amount of an mGlu5 negative allosteric modulator (NAM) or a pharmaceutically acceptable salt thereof, wherein the mGlu5 NAM is a compound of Formula I:

(I)

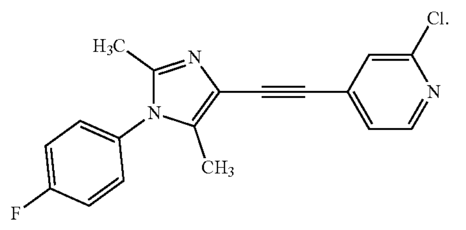

The details of one or more embodiments of the disclosure are set forth in the description below. Other features, objects, and advantages of the disclosure will be apparent from the below drawings, description and from the claims.

DETAILED DESCRIPTION

Figure 1:
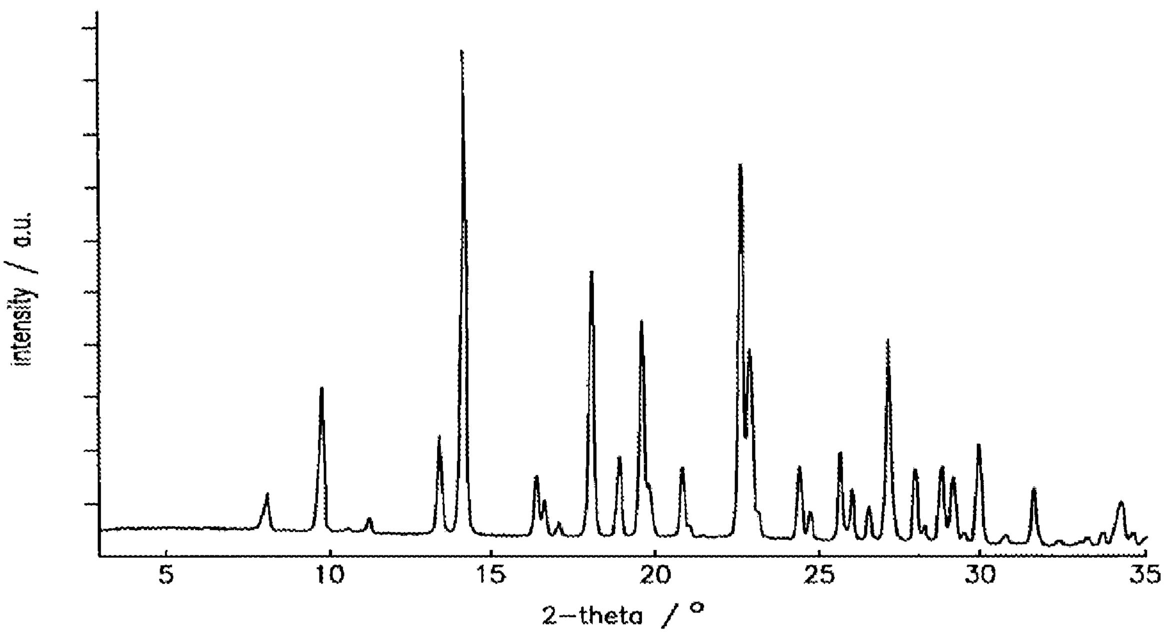
FIG. 1 depicts an exemplary XRPD pattern of a crystalline anhydrate form (Form A) of a monosulfate of the compound of Formula I.

As generally described herein, the present disclosure provides methods of treating medical conditions associated with tuberous sclerosis complex (TSC) in a subject in need thereof. The present disclosure also describes treating medical conditions associated with TSC by using certain crystalline forms of pharmaceutically acceptable salts of the compound of Formula I. In addition, the present disclosure provides a solid form of a crystalline anhydrate form (Form A) of a monosulfate salt of the compound of Formula I, wherein the solid form has a particle size (Dv50) of less than or equal to about 100 μm (e.g., less than 47 μm, or 10 μm or less).

Definitions

To facilitate an understanding of the present invention, a number of terms and phrases are defined below.

Unless defined otherwise, all technical and scientific terms used herein have the same meaning as commonly understood by one of ordinary skill in the art to which this invention belongs. Unless defined otherwise, all abbreviations used herein have their conventional meaning within the chemical and biological arts. The chemical structures and formulae set forth herein are constructed according to the standard rules of chemical valency known in the chemical arts.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from the group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

The articles "a" and "an" are used in this disclosure to refer to one or more than one (i.e., at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "comprise," "comprises," "comprising," "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred from the context.

At various places in the present specification, variable or parameters are disclosed in groups or in ranges. It is specifically intended that the description include each and every individual subcombination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

As a general matter, compositions specifying a percentage are by weight unless otherwise specified. Further, if a variable is not accompanied by a definition, then the previous definition of the variable controls.

As used herein, "composition" or "pharmaceutical composition" or "pharmaceutical formulation" refers to the combination of an active agent with an excipient or a carrier, inert or active, making the composition especially suitable for diagnostic or therapeutic use in vivo or ex vivo.

"Pharmaceutically acceptable" refers to compounds, molecular entities, compositions, materials and/or dosage forms that do not produce an adverse, allergic or other untoward reaction when administered to an animal, or a human, as appropriate, and/or that are approved or approvable by a regulatory agency of the federal or a state government or the corresponding agency in countries other than the United States, or that is listed in the U.S. Pharmacopoeia or other generally recognized pharmacopoeia for use in animals, and more particularly, in humans.

As used herein, "pharmaceutically acceptable salt" refers to any salt of an acidic or a basic group that may be present in a compound of the present invention (e.g., the compound of Formula I), which salt is compatible with pharmaceutical administration.

Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acid. Other acids, such as oxalic, while not in themselves pharmaceutically acceptable, may be employed in the preparation of salts useful as intermediates in obtaining the compounds described herein and their pharmaceutically acceptable acid addition salts.

Examples of bases include, but are not limited to, alkali metal (e.g., sodium and potassium) hydroxides, alkaline earth metal (e.g., magnesium and calcium) hydroxides, ammonia, and compounds of formula $NW_4^+$, wherein W is $C_{1-4}$ alkyl, and the like.

Examples of salts include, but are not limited, to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, monosulfate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $K^+$, $Ca^{2+}$, $NH_4^+$, and $NW_4^+$ (where W can be a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, "pharmaceutically acceptable excipient" refers to a substance that aids the administration of an active agent to and/or absorption by a subject and can be included in the compositions of the present invention without causing a significant adverse toxicological effect on the patient. Non-limiting examples of pharmaceutically acceptable excipients include water, NaCl, normal saline solutions, such as a phosphate buffered saline solution, emulsions (e.g., such as an oil/water or water/oil emulsions), lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. For examples of excipients, see Martin, Remington's Pharmaceutical Sciences, 15th Ed., Mack Publ. Co., Easton, PA (1975).

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

As used herein, "solid dosage form" means a pharmaceutical dose(s) in solid form, e.g., tablets, capsules, granules, powders, sachets, reconstitutable powders, dry powder inhalers and chewables.

As used herein, "administering" means oral administration, administration as a suppository, topical contact, intravenous administration, parenteral administration, intraperitoneal administration, intramuscular administration, intralesional administration, intrathecal administration, intracranial administration, intranasal administration, transmucosal administration (e.g., buccal, sublingual, nasal, or transdermal), or subcutaneous administration, or the implantation of a slow-release device, e.g., a mini-osmotic pump, to a subject. Parenteral administration includes, e.g., intravenous, intramuscular, intra-arterial, intradermal, subcutaneous, intraperitoneal, intraventricular, and intracranial. Other modes of delivery include, but are not limited to, the use of liposomal formulations, intravenous infusion, transdermal patches, etc.

By "co-administer," it is meant that a composition described herein is administered at the same time, just prior to, or just after the administration of one or more additional therapies (e.g., anti-cancer agent, chemotherapeutic, or treatment for a neurodegenerative disease). The compound of Formula I, or a pharmaceutically acceptable salt thereof, can be administered alone or can be co-administered to the patient. Co-administration is meant to include simultaneous or sequential administration of the compound individually or in combination (more than one compound or agent). Thus, the preparations can also be combined, when desired, with other active substances (e.g., to reduce metabolic degradation).

As used herein, and unless otherwise specified, the terms "treat," "treating" and "treatment" include an action that occurs while a subject is suffering from the specified disease, disorder or condition, which reduces the severity of the disease, disorder or condition, or retards or slows the progression of the disease, disorder or condition (e.g., "therapeutic treatment"). "Treat," "treating" and "treatment", as used herein, can include any effect, for example, lessening, reducing, modulating, ameliorating, or eliminating, that results in the improvement of the condition, disease, disorder, and the like, including one or more symptoms thereof. Treating can be curing, improving, or at least partially ameliorating the disorder.

The phrase "therapeutically effective amount," as used herein, refers to the amount of a compound (e.g., a compound of Formula I), or a pharmaceutically acceptable salt thereof, that will elicit the biological or medical response of a tissue, system, animal or human that is being sought by the researcher, veterinarian, medical doctor or other clinician. The compound, or a pharmaceutically acceptable salt thereof, described in the present disclosure can be administered in therapeutically effective amounts to treat a disease. A therapeutically effective amount of a compound, or a pharmaceutically acceptable salt thereof, can be the quantity required to achieve a desired therapeutic and/or prophylactic effect, such as an amount which results in lessening of a symptom of a disease such as TSC.

Tuberous sclerosis complex (TSC) is a rare, multi-system genetic disease that causes benign tumors to grow in the brain and on other vital organs such as the kidneys, heart, eyes, lungs, and skin. TSC usually affects the central nervous system and results in a combination of symptoms including seizures, developmental delay, behavioral problems, skin abnormalities, and kidney disease. See e.g., https://www.ninds.nih.gov/Disorders/Patient-Caregiver-Education/Fact-Sheets/Tuberous-Sclerosis-Fact-Sheet.

Compound

The compound of Formula I, as depicted below, is an mGlu5 negative allosteric modulator (NAM), also known as 2-chloro-4-[1-(4-fluorophenyl)-2,5-dimethyl-1H-imidazol-4-ylethynyl]pyridine:

(I)

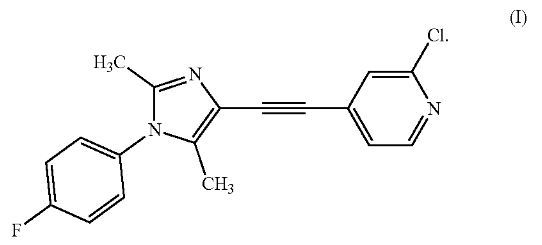 [SMILES: Cc1nc(C#Cc2ccnc(Cl)c2)c(C)n1-c1ccc(F)cc1]

A method of chemically synthesizing the compound of Formula I (including Example 1 provided herein) is described in U.S. Pat. No. 7,332,510, which is incorporated by reference in its entirety.

It should be understood that the compound of Formula I as described herein includes crystalline solid forms of either the free base or pharmaceutically acceptable salts of the compound of Formula I as described herein.

In certain embodiments, the pharmaceutically acceptable salt of the compound of Formula I can be a salt of the compound of Formula I with physiologically compatible mineral acids, such as hydrochloric acid, sulfuric (or sulphuric) acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. An exemplary pharmaceutically acceptable salt of the compound of Formula I is a monosulfate salt or a hemisulfate salt.

In certain embodiments, the pharmaceutically acceptable salt of the compound of Formula I is a monosulfate salt or a hemisulfate salt, each being in hydrate or anhydrate form (e.g., anhydrate, hemihydrate, or monohydrate).

In certain embodiments, the pharmaceutically acceptable salt of the compound of Formula I is in a crystalline form or an amorphous form.

In some embodiments, the compound is in a crystalline anhydrate form (Form A) of a monosulfate salt of the compound of Formula I, wherein Form A has an X-ray powder diffraction (XRPD) pattern as substantially shown in FIG. 1. In some embodiments, Form A is characterized by at least three peaks selected from the following X-ray powder diffraction peaks obtained with a $Cu_{K\alpha}$ radiation at 2θ (2 Theta): 9.8±0.2°, 13.4±0.2°, 14.2±0.2°, 18.1±0.2°, 18.9±0.2°, 19.6±0.2°, 22.6±0.2°, 22.9±0.2°, 25.7±0.2°, 27.1±0.2°, and 29.9±0.2°. The crystalline Form A typically has a $T_m$ of about 180-190° C. by DSC analysis. In some embodiments, Form A is characterized by an infrared spectrum having sharp bands at 3068, 2730, 2618, 2236, 2213, 1628, 1587, 1569, 1518, 1384, 1374, 1295, 1236, 1168, 1157, 1116, 1064, 1019, 902, 855, 786, and 674 $cm^{-1}$ (±3 $cm^{-1}$).

Figure 2:
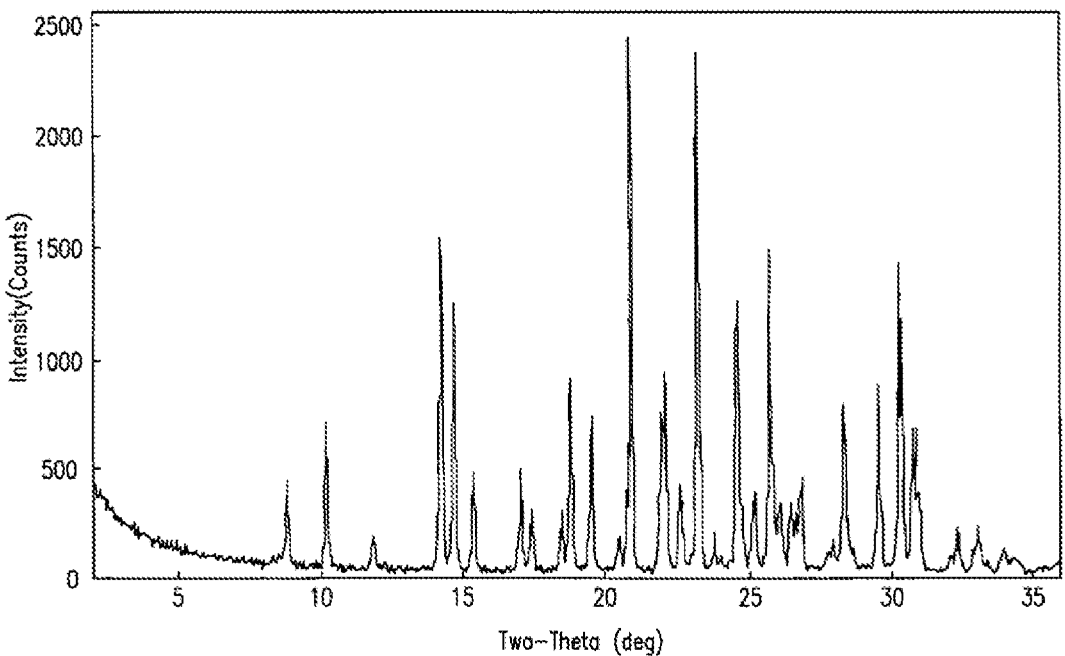
FIG. 2 depicts an exemplary XRPD pattern of a crystalline monohydrate form (Form B) of a monosulfate of the compound of Formula I.

In some embodiments, the compound is in a crystalline monohydrate form (Form B) of a monosulfate salt of the compound of Formula I, wherein Form B has an XRPD pattern as substantially shown in FIG. 2. The crystalline Form B typically has a $T_m$ of about 60-70° C. by DSC analysis.

Figure 3:
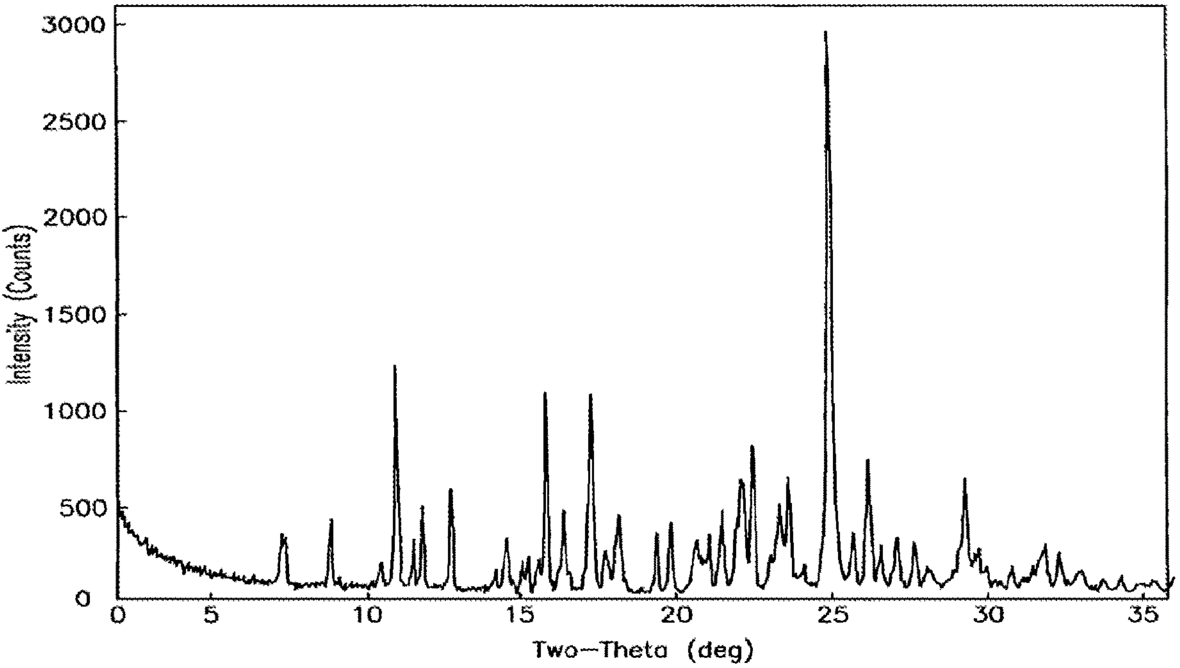
FIG. 3 depicts an exemplary XRPD pattern of a crystalline hemihydrate form (Form C) of a hemisulfate of the compound of Formula I.

In some embodiments, the compound is in a crystalline hemihydrate form (Form C) of a hemisulfate salt of the compound of Formula I, wherein Form C has an XRPD pattern as substantially shown in FIG. 3. The crystalline Form C typically has a $T_m$ of about 90-100° C. by DSC analysis.

Pharmaceutical Compositions

In one aspect, the present disclosure relates to a composition such as a pharmaceutical composition comprising the compound of Formula I, or a pharmaceutically acceptable salt thereof, and a pharmaceutically acceptable excipient, for the treatment of TSC in a subject in need thereof. In various embodiments, the composition is a solid pharmaceutical composition.

In various embodiments, the amount of the compound of Formula I, or a pharmaceutically acceptable salt thereof, in the pharmaceutical compositions described herein can be from about 0.01 mg to about 30 mg, about 0.05 mg to about 20 mg, about 0.1 mg to about 10 mg, about 0.5 mg to about 10 mg, about 1 mg to about 10 mg, about 2 mg to about 10 mg, about 3 mg to about 10 mg, about 4 mg to about 10 mg, about 5 mg to about 10 mg, about 6 mg to about 10 mg, about 7 mg to about 10 mg, about 8 mg to about 10 mg, about 9 mg to about 10 mg, about 1 mg to about 9 mg, about 1 mg to about 8 mg, about 1 mg to about 7 mg, about 1 mg to about 6 mg, about 1 mg to about 5 mg, about 1 mg to about 4.5 mg, about 1 mg to about 4 mg, about 1 mg to about 3.5 mg, about 1 mg to about 3 mg, about 1 mg to about 2.5 mg, about 1 mg to about 2 mg, about 1 mg to about 1.5 mg, about 1.5 mg to about 9 mg, about 1.5 mg to about 8 mg, about 1.5 mg to about 7 mg, about 1.5 mg to about 6 mg, about 1.5 mg to about 5 mg, about 1.5 mg to about 4.5 mg, about 1.5 mg to about 4 mg, about 1.5 mg to about 3.5 mg, about 1.5 mg to about 3 mg, about 1.5 mg to about 2.5 mg, about 1.5 mg to about 2 mg, about 2 mg to about 9 mg, about 2 mg to about 8 mg, about 2 mg to about 7 mg, about 2 mg to about 6 mg, about 2 mg to about 5 mg, about 2 mg to about 4.5 mg, about 2 mg to about 4 mg, about 2 mg to about 3.5 mg, about 2 mg to about 3 mg, about 2 mg to about 2.5 mg, about 2.5 mg to about 9 mg, about 2.5 mg to about 8 mg, about 2.5 mg to about 7 mg, about 2.5 mg to about 6 mg, about 2.5 mg to about 5 mg, about 2.5 mg to about 4.5 mg, about 2.5 mg to about 4 mg, about 2.5 mg to about 3.5 mg, about 2.5 mg to about 3 mg, about 3 mg to about 9 mg, about 3 mg to about 8 mg, about 3 mg to about 7 mg, about 3 mg to about 6 mg, about 3 mg to about 5 mg, about 3 mg to about 4.5 mg, about 3 mg to about 4 mg, about 3 mg to about 3.5 mg, about 3.5 mg to about 9 mg, about 3.5 mg to about 8 mg, about 3.5 mg to about 7 mg, about 3.5 mg to about 6 mg, about 3.5 mg to about 5 mg, about 3.5 mg to about 4.5 mg, about 3.5 mg to about 4 mg, about 4 mg to about 9 mg, about 4 mg to about 8 mg, about 4 mg to about 7 mg, about 4 mg to about 6 mg, about 4 mg to about 5 mg, about 4 mg to about 4.5 mg, about 4.5 mg to about 9 mg, about 4.5 mg to about 8 mg, about 4.5 mg to about 7 mg, about 4.5 mg to about 6 mg, about 4.5 mg to about 5 mg, about 5 mg to about 9 mg, about 5 mg to about 8 mg, about 5 mg to about 7 mg, about 5 mg to about 6 mg, about 6 mg to about 9 mg, about 6 mg to about 8 mg, about 6 mg to about 7 mg, about 7 mg to about 9 mg, about 7 mg to about 8 mg, or about 8 mg to about 9 mg.

In certain embodiments, the amount of the compound of Formula I, or a pharmaceutically acceptable salt thereof, in the pharmaceutical compositions described herein can be from about 0.1 mg to about 1.5 mg.

In various embodiments, the amount of the compound of Formula I, or a pharmaceutically acceptable salt thereof, in the pharmaceutical compositions described herein can be about 0.1 mg, about 0.2 mg, about 0.3 mg, about 0.4 mg, about 0.5 mg, about 1.0 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, or about 10 mg.

In certain embodiments, the amount of the compound of Formula I, or a pharmaceutically acceptable salt thereof, in the pharmaceutical compositions described herein can be about 0.1 mg to about 0.2 mg (e.g., about 0.13 mg).

In certain embodiments, the amount of the compound of Formula I, or a pharmaceutically acceptable salt thereof, in the pharmaceutical compositions described herein can be about 0.2 mg to about 0.3 mg (e.g., about 0.26 mg).

In certain embodiments, the amount of the compound of Formula I, or a pharmaceutically acceptable salt thereof, in the pharmaceutical compositions described herein can be about 0.6 mg to about 0.7 mg (e.g., about 0.65 mg).

In certain embodiments, the amount of the compound of Formula I, or a pharmaceutically acceptable salt thereof, in the pharmaceutical compositions described herein can be about 1.2 mg to about 1.4 mg (e.g., about 1.3 mg).

In certain embodiments, the amount of the compound of Formula I, or a pharmaceutically acceptable salt thereof, in the pharmaceutical compositions described herein can be about 1 mg to about 4 mg. In certain embodiments, the amount of the compound of Formula I, or a pharmaceutically acceptable salt thereof, in the pharmaceutical compositions described herein can be about 1 mg to about 3 mg. In certain embodiments, the amount of the compound of Formula I, or a pharmaceutically acceptable salt thereof, in the pharmaceutical compositions described herein can be about 1.5 mg to about 4.5 mg. In certain embodiments, the amount of the compound of Formula I, or a pharmaceutically acceptable salt thereof, in the pharmaceutical compositions described herein can be about 1.5 mg to about 3.5 mg. In certain embodiments, the amount of the compound of Formula I, or a pharmaceutically acceptable salt thereof, in the pharmaceutical compositions described herein can be about 3.5 mg, about 3.0 mg, about 2.5 mg, about 2.0 mg, about 1.5 mg, or about 1.0 mg. In certain embodiments, the amount of the compound of Formula I, or a pharmaceutically acceptable salt thereof, in the pharmaceutical compositions described herein can be about 5.0 mg, about 4.5 mg, about 4.0 mg, about 3.5 mg, about 3.0 mg, about 2.5 mg, about 2.0 mg, about 1.5 mg, about 1.0 mg, or about 0.5 mg.

In some embodiments, the compound of Formula I, or a pharmaceutically acceptable salt thereof, is present in the composition in an amount from about 0.01% to about 20% by weight, about 0.05% to about 15% by weight, about 0.1% to about 10% by weight, about 0.1% to about 5% by weight, about 0.1% to about 1% by weight, or about 0.1% to about 0.5% by weight, based on the total weight of the composition.

In some embodiments, the compound of Formula I, or a pharmaceutically acceptable salt thereof, is present in the composition in an amount from about 0.05% to about 15% by weight.

In some embodiments, the compound of Formula I, or a pharmaceutically acceptable salt thereof, is present in the composition in an amount from about 0.1% to about 0.5% by weight.

In various embodiments, the pharmaceutical compositions described herein comprise a therapeutically effective amount of a pharmaceutically acceptable salt of the compound of Formula I. In some embodiments, the pharmaceutically acceptable salt of the compound of Formula I can be a salt of the compound of Formula I with physiologically compatible mineral acids, such as hydrochloric acid, sulfuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid.

In certain embodiments, the pharmaceutically acceptable salt of the compound of Formula I is a monosulfate salt or a hemisulfate salt, each being in hydrate or anhydrate form (e.g., anhydrate, hemihydrate, or monohydrate).

In certain embodiments, the pharmaceutically acceptable salt of the compound of Formula I is in a crystalline form or an amorphous form.

In certain embodiments, the pharmaceutical compositions described herein comprise a crystalline anhydrate form (Form A) of a monosulfate salt of the compound of Formula I, wherein Form A has an X-ray powder diffraction (XRPD) pattern as substantially shown in FIG. 1. The crystalline Form A typically has a $T_m$ of about 180-190° C. by DSC analysis (e.g., 180±1° C., 182±1° C., 184±1° C., 186±1° C., 188±1° C., or 190±1° C.).

In some embodiments, the pharmaceutical compositions described herein comprise a crystalline monohydrate form (Form B) of a monosulfate salt of the compound of Formula I, wherein Form B has an XRPD pattern as substantially shown in FIG. 2. The crystalline Form B typically has a $T_m$ of about 60-70° C. by DSC analysis (e.g., 60±1° C., 62±1° C., 64±1° C., 66±1° C., 68±1° C., or 70±1° C.).

In some embodiments, the pharmaceutical compositions described herein comprise a crystalline hemihydrate form (Form C) of a hemisulfate salt of the compound of Formula I, wherein Form C has an XRPD pattern as substantially shown in FIG. 3. The crystalline Form C typically has a $T_m$ of about 90-100° C. by DSC analysis (e.g., 90±1° C., 92±1° C., 94±1° C., 96±1° C., 98±1° C., or 100±1° C.).

In certain embodiments, the pharmaceutical compositions described herein comprise an amorphous form of a monosulfate salt of the compound of Formula I, wherein said amorphous form is characterized by an infrared spectrum having bands at 2730, 2592, 2219, 1633, 1586, 1570, 1513, 1375, 1343, 1293, 1226, 1157, 1130, 1084, 1040, 986, 903, 848, 788, 712 and 670 $cm^{-1}$ (±3 $cm^{-1}$).

In some embodiments, the pharmaceutical composition is a tablet formulation such as a modified release tablet formulation, or a matrix pellet formulation such as a modified release matrix pellet formulation, which can be encapsulated in a capsule. A "modified release formulation," or a "modified-release dosage," as used herein, refers to a mechanism that (in contrast to immediate-release dosage) delivers a drug with a delay after its administration (delayed-release dosage), or for a prolonged period of time (extended-release dosage). See, Perrie et al., Pharmaceutics: Drug Delivery and Targeting ($2^{nd}$), 2012, 7-13.

In certain embodiments, the pharmaceutical composition is a modified release matrix pellet formulation encapsulated in a capsule, wherein the compound of Formula I, or a pharmaceutically acceptable salt thereof, is present in an amount from about 0.05 mg to about 20 mg (e.g., about 0.1 mg to about 0.2 mg, about 0.2 mg to about 0.3 mg, about 0.6 mg to about 0.7 mg, or about 1.2 mg to about 1.4 mg).

In certain embodiments, the pharmaceutical composition is a modified release pellet formulation encapsulated in a capsule, wherein the compound of Formula I, or a pharmaceutically acceptable salt thereof, is present in the composition in an amount from about 0.01% to about 20% by weight (e.g., about 0.05% to about 15% by weight, about 0.1% to about 1% by weight, or about 0.1% to about 0.5% by weight), based on the total weight of the composition.

In certain embodiments, the pharmaceutical composition described herein comprises a crystalline anhydrate form (Form A) of a monosulfate salt of the compound of Formula I, wherein Form A has an XRPD pattern as substantially shown in FIG. 1; and the Form A monosulfate salt is present in the composition in an amount from about 0.05 mg to about 20 mg (e.g., about 0.1 mg to about 0.2 mg, about 0.2 mg to about 0.3 mg, about 0.6 mg to about 0.7 mg, or about 1.2 mg to about 1.4 mg).

In certain embodiments, the pharmaceutical composition described herein comprises a crystalline anhydrate form (Form A) of a monosulfate salt of the compound of Formula I, wherein Form A has an XRPD pattern as substantially shown in FIG. 1; and the Form A monosulfate salt is present in the composition in an amount from about 0.01% to about 20% by weight (e.g., about 0.05% to about 15% by weight, about 0.1% to about 1% by weight, or about 0.1% to about 0.5% by weight), based on the total weight of the composition.

As described herein, the present disclosure includes a solid pharmaceutical composition comprising a solid form of a compound of Formula I, namely, a crystalline anhydrate form (Form A) of a monosulfate salt of the compound of Formula I; where the composition is in the form of a matrix pellet and the solid form has a mean particle size (Dv50) of less than or equal to about 100 μm. The Dv50 can be determined by a LA-950 laser diffraction method. See, e.g., https://static.horiba.com/fileadmin/Horiba/Products/Scientific/Particle_Characterization/Downloads/Technical_Notes/TN159_LA-950_Laser_Diffraction_Technique.pdf.

In various embodiments, the pharmaceutical composition comprises a matrix pellet of the solid form having a particle size of less than 47 μm, less than 45 μm, less than 40 μm, less than 35 μm, less than 30 μm, less than 25 μm, less than 20 μm, less than 15 μm, less than 10 μm, or less than 5 μm. In certain embodiments, the solid form has a particle size of about 10 μm or less (e.g., about 10 μm, about 9 μm, about 8 μm, about 7 μm, about 6 μm, about 5 μm, about 4 μm, about 3 μm, about 2 μm, or about 1 μm).

In certain embodiments, the solid form has a particle size of less than 47 μm and the Form A monosulfate salt is present in the composition in an amount of 1% by weight or less, based on the total weight of the composition.

In certain embodiments, the solid form has a particle size of about 10 μm or less (e.g., about 3.3 μm), and the Form A monosulfate salt is present in the composition in an amount of 0.5% by weight or less (e.g., 0.1% by weight), based on the total weight of the composition.

In certain embodiments, the pharmaceutical composition comprises comprises a pharmaceutical excipient comprising a polymer, a binder, a disintegrant, a lubricant, or a glidant.

In certain embodiments, the polymer is a matrix forming polymer (e.g., microcrystalline cellulose), a pH-responding polymer (e.g., methacrylic acid copolymer), or a binder (e.g., hypromellose). In certain embodiments, the polymer is one or more polymers selected from the group consisting of a cellulose such as microcrystalline cellulose, methacrylic acid copolymer, and hypromellose. In certain embodiments, the glidant is talc.

The pharmaceutical compositions provided herein can be administered by a variety of routes including, but not limited to, oral administration, administration as a suppository, topical contact, parenteral administration (e.g., intravenous, intramuscular, intra-arterial, intradermal, subcutaneous, intraperitoneal, intraventricular, and intracranial), intralesional administration, intrathecal administration, intranasal administration, transmucosal administration (e.g., buccal, sublingual, nasal, or transdermal), or the implantation of a slow-release device, e.g., a mini-osmotic pump, to a subject. In certain embodiments, the pharmaceutical compositions disclosed herein are administered orally.

The pharmaceutical compositions provided herein may also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions provided herein may be presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. In various embodiments, the pharmaceutical dosage forms described herein can be administered as a unit dose. Typical unit dosage forms include prefilled, premeasured ampules or syringes of the liquid compositions or pills, tablets, capsules or the like in the case of solid compositions.

In certain embodiments, the pharmaceutical compositions provided herein are administered to the patient as a solid dosage form. In certain embodiments, the solid dosage form is a capsule (e.g., a modified release pellet formulation encapsulated in a capsule). In certain embodiments, the solid dosage form is a tablet (e.g., a modified release tablet formulation).

In certain embodiments, the pharmaceutical compositions provided herein comprise the compound of Formula I as the sole active agent, or in combination with other active agents.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* $21^{st}$ ed., Lippincott Williams & Wilkins, 2005.

Methods of Use and Treatment

In one aspect, provided herein are methods of treating a medical condition associated with tuberous sclerosis complex (TSC) in a subject (e.g., a human) in need thereof.

In various embodiments, provided herein are methods for treating a medical condition associated with TSC in a subject in need thereof, comprising administering to a subject in need thereof a composition comprising a therapeutically effective amount of a compound or a pharmaceutically acceptable salt thereof, wherein the compound is of Formula I:

(I)

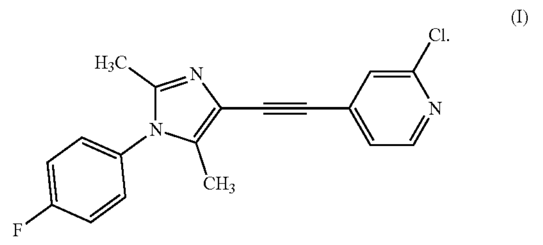 [SMILES: Cc1nc(C#Cc2ccnc(Cl)c2)c(C)n1-c1ccc(F)cc1]

In certain embodiments, provided herein are methods of treating tuberous sclerosis complex, comprising administering to a subject in need thereof a composition comprising a therapeutically effective amount of an mGlu5 negative allosteric modulator (NAM), or a pharmaceutically acceptable salt thereof, wherein the mGlu5 NAM is a compound of Formula I:

(I)

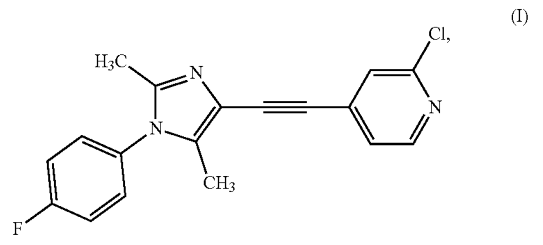 [SMILES: Cc1nc(C#Cc2ccnc(Cl)c2)c(C)n1-c1ccc(F)cc1]

wherein administering comprises administering the compound of Formula I, or a pharmaceutically acceptable salt thereof, in an amount of about 1.5 mg to about 3.5 mg once daily. In some embodiments, the subject has a weight of at least 40 kg. In some embodiments, the subject has a weight of less than 40 kg.

In certain embodiments, provided herein are methods of treating tuberous sclerosis complex, comprising administering to a subject in need thereof a composition comprising a therapeutically effective amount of an mGlu5 negative allosteric modulator (NAM), or a pharmaceutically acceptable salt thereof, wherein the mGlu5 NAM is a compound of Formula I:

(I)

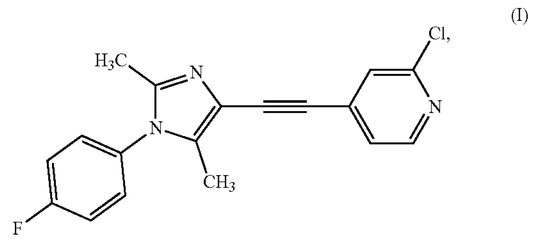 [SMILES: Cc1nc(C#Cc2ccnc(Cl)c2)c(C)n1-c1ccc(F)cc1]

wherein administering comprises administering the compound of Formula I, or a pharmaceutically acceptable salt thereof, in an amount of about 1.0 mg to about 3.0 mg once daily. In some embodiments, the subject has a weight of at least 40 kg. In some embodiments, the subject has a weight of less than 40 kg.

In various embodiments, administering a therapeutically effective amount of the compound of Formula I, or a pharmaceutically acceptable salt thereof, comprises administering to a subject from about 0.05 mg to about 20 mg (e.g., about 0.1 mg, about 0.2 mg, about 0.3 mg, about 0.4 mg, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, or about 10 mg) of the compound of Formula I, or a pharmaceutically acceptable salt thereof.

In certain embodiments, administering a therapeutically effective amount of the compound of Formula I, or a pharmaceutically acceptable salt thereof, comprises administering from about 0.1 mg to about 1.5 mg of the compound of Formula I, or a pharmaceutically acceptable salt thereof, to a subject in need thereof.

In certain embodiments, administering a therapeutically effective amount of the compound of Formula I, or a pharmaceutically acceptable salt thereof, comprises administering from about 0.1 mg to about 4 mg (e.g., from about 0.1 mg to about 3.8 mg, from about 0.1 mg to about 3.6 mg, from about 0.1 mg to about 3.4 mg, from about 0.1 mg to about 3.2 mg, from about 0.1 mg to about 3.0 mg, from about 0.1 mg to about 2.8 mg, from about 0.1 to about 2.6 mg, from about 0.1 mg to about 2.4 mg, from about 0.1 mg to about 2.2 mg, from about 0.1 mg to about 2.0 mg, from about 0.1 mg to about 1.8 mg, from about 0.1 mg to about 1.6 mg, from about 0.1 mg to about 1.4 mg, from about 0.1 mg to about 1.2 mg, from about 0.1 mg to about 1.0 mg, from about 0.1 mg to about 0.8 mg, from about 0.1 mg to about 0.6 mg, from about 0.1 mg to about 0.4 mg, from about 0.1 mg to about 0.2 mg, from about 0.2 mg to about 4 mg, from about 0.2 mg to about 3.5 mg, about 0.5 mg to about 3.5 mg, about 0.5 mg to about 4 mg, or about 1 mg to about 4 mg) of the compound of Formula I, or a pharmaceutically acceptable salt thereof, to a subject in need thereof. In certain embodiments, the administering is once daily.

In certain embodiments, administering a therapeutically effective amount of the compound of Formula I, or a pharmaceutically acceptable salt thereof, comprises administering from about 0.1 mg to about 3 mg (e.g., about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, or about 3.0 mg) of the compound of Formula I, or a pharmaceutically acceptable salt thereof, to a subject in need thereof. In certain embodiments, the administering is once daily.

In certain embodiments, administering a therapeutically effective amount of the compound of Formula I, or a pharmaceutically acceptable salt thereof, comprises administering from about 0.1 mg to about 3.5 mg (e.g., about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, or about 3.5 mg) of the compound of Formula I, or a pharmaceutically acceptable salt thereof, to a subject in need thereof. In certain embodiments, the administering is once daily.

In certain embodiments, administering a therapeutically effective amount of the compound of Formula I, or a pharmaceutically acceptable salt thereof, comprises administering about 1.0 mg to about 5.0 mg (e.g., about 1.0 mg to about 4.9 mg, about 1.0 mg to about 4.8 mg, about 1.0 mg to about 4.7 mg, about 1.0 mg to about 4.6 mg, about 1.0 mg to about 4.5 mg, about 1.0 mg to about 4.4 mg, about 1.0 mg to about 4.3 mg, about 1.0 mg to about 4.2 mg, about 1.0 mg to about 4.1 mg, about 1.0 mg to about 4.0 mg, about 1.0 mg to about 3.9 mg, about 1.0 mg to about 3.8 mg, about 1.0 mg to about 3.7 mg, and about 1.0 mg to about 3.6 mg) of the compound of Formula I, or a pharmaceutically acceptable salt thereof, to a subject in need thereof.

In certain embodiments, administering a therapeutically effective amount of the compound of Formula I, or a pharmaceutically acceptable salt thereof, comprises administering about 1.0 mg to about 3.0 mg of the compound of Formula I, or a pharmaceutically acceptable salt thereof, to a subject in need thereof. In embodiments, administering a therapeutically effective amount of the compound of Formula I, or a pharmaceutically acceptable salt thereof, comprises administering about 0.5 mg to about 3.0 mg of the compound of Formula I, or a pharmaceutically acceptable salt thereof, to a subject in need thereof. In embodiments, administering a therapeutically effective amount of the compound of Formula I, or a pharmaceutically acceptable salt thereof, comprises administering about 1.0 mg to about 3.5 mg of the compound of Formula I, or a pharmaceutically acceptable salt thereof, to a subject in need thereof. In embodiments, administering a therapeutically effective amount of the compound of Formula I, or a pharmaceutically acceptable salt thereof, comprises administering about 1.0 mg to about 4 mg of the compound of Formula I, or a pharmaceutically acceptable salt thereof, to a subject in need thereof. In various embodiments, the administering is once daily.

In certain embodiments, administering a therapeutically effective amount of the compound of Formula I, or a pharmaceutically acceptable salt thereof, comprises administering about 1.5 mg to about 3.5 mg of the compound of Formula I, or a pharmaceutically acceptable salt thereof, to a subject in need thereof. In certain embodiments, the administering is once daily. In certain embodiments, administering a therapeutically effective amount of the compound of Formula I, or a pharmaceutically acceptable salt thereof, comprises administering about 1.5 mg to about 4.0 mg of the compound of Formula I, or a pharmaceutically acceptable salt thereof, to a subject in need thereof. In embodiments, the administering is once daily. In certain embodiments, administering a therapeutically effective amount of the compound of Formula I, or a pharmaceutically acceptable salt thereof, comprises administering about 1.5 mg to about 4.5 mg of the compound of Formula I, or a pharmaceutically acceptable salt thereof, to a subject in need thereof. In embodiments, administering a therapeutically effective amount of the compound of Formula I, or a pharmaceutically acceptable salt thereof, comprises administering about 1.0 mg to about 3.5 mg of the compound of Formula I, or a pharmaceutically acceptable salt thereof, to a subject in need thereof. In embodiments, administering a therapeutically effective amount of the compound of Formula I, or a pharmaceutically acceptable salt thereof, comprises administering about 0.5 mg to about 3.5 mg of the compound of Formula I, or a pharmaceutically acceptable salt thereof, to a subject in need thereof. In various embodiments, the administering is once daily.

In certain embodiments, administering a therapeutically effective amount of the compound of Formula I, or a pharmaceutically acceptable salt thereof, comprises administering about about 3.5 mg, about 3.0 mg, about 2.5 mg, about 2.0 mg, about 1.5 mg, or about 1.0 mg of the compound of Formula I, or a pharmaceutically acceptable salt thereof, to a subject in need thereof. In certain embodiments, the administering is once daily. In certain embodiments, administering a therapeutically effective amount of the compound of Formula I, or a pharmaceutically acceptable salt thereof, comprises administering about about 6.0 mg, 5.5 mg, 5.0 mg, 4.5 mg, 4.0 mg, 3.5 mg, about 3.0 mg, about 2.5 mg, about 2.0 mg, about 1.5 mg, about 1.0 mg, or about 0.5 mg of the compound of Formula I, or a pharmaceutically acceptable salt thereof, to a subject in need thereof. In certain embodiments, the administering is once daily.

In certain embodiments, administering a therapeutically effective amount of the compound of Formula I, or a pharmaceutically acceptable salt thereof, comprises administering once daily about 3 mg of the compound of Formula I, or a pharmaceutically acceptable salt thereof, to a subject in need thereof. In some embodiments, the subject has a weight less than 40 kg. In certain embodiments, administering a therapeutically effective amount of the compound of Formula I, or a pharmaceutically acceptable salt thereof, comprises administering once daily about 3.5 mg of the compound of Formula I, or a pharmaceutically acceptable salt thereof, to a subject in need thereof. In some embodiments, the subject has a weight less than 40 kg. In certain embodiments, administering a therapeutically effective amount of the compound of Formula I, or a pharmaceutically acceptable salt thereof, comprises administering once daily about 4.0 mg of the compound of Formula I, or a pharmaceutically acceptable salt thereof, to a subject in need thereof.

In some embodiments, the subject has a weight less than about 40 kg. In some embodiments, the subject has a weight equal to or more than about 40 kg (e.g., about 40 kg, about 45 kg, about 50 kg, about 55 kg, about 60 kg, about 65 kg, about 70 kg, about 75 kg, about 80 kg, about 85 kg, about 90 kg, about 95 kg, about 100 kg, about 105 kg, about 110 kg, about 115 kg, about 120 kg, about 125 kg, about 130 kg, about 135 kg, about 140 kg, about 145 kg). In some embodiments, the subject weighs at least about 40 kg (e.g., about 38 kg, about 36 kg, about 34 kg, about 32 kg, about 30 kg, about 28 kg, about 26 kg, about 24 kg, about 22 kg, about 20 kg, about 18 kg, about 16 kg, about 14 kg, about 12 kg, about 10 kg, about 8 kg, about 6 kg, about 4 kg, about 2 kg). In embodiment, the subject has a weight of about 1 kg to about 40 kg (e.g., about 5 kg to about 40 kg, about 10 kg to about 40 kg, about 15 kg to about 40 kg, about 20 kg to about 40 kg, about 25 kg to about 40 kg, about 30 kg to about 40 kg, about 35 kg to about 40 kg). In embodiment, the subject has a weight of about 41 kg to about 100 kg (about 40 kg to about 100 kg, about 45 kg to about 100 kg, about 50 kg to about 100 kg, about 55 kg to about 100 kg, about 60 kg to about 100 kg, about 40 kg to about 45 kg, about 40 kg to about 50 kg, about 40 kg to about 55 kg, about 40 kg to about 60 kg, about 40 kg to about 65 kg, about 40 kg to about 70 kg, about 40 kg to about 80 kg, about 40 kg to about 90 kg). In some embodiments, the subject weighs at least about 35 kg, about 30 kg, about 25 kg, about 20 kg, about 15 kg, about 10 kg, or about 5 kg.

In certain embodiments, provided herein is a method of administering the free base form of the compound of Formula I for the treatment of medical conditions associated with TSC in a subject in need thereof.

In certain embodiments, provided herein is a method of administering a pharmaceutically acceptable salt of the compound of Formula I for the treatment of medical conditions associated with TSC in a subject in need thereof.

In certain embodiments, treating comprises administering the compound of Formula I, or a pharmaceutically acceptable salt thereof, once, twice, three, four, or five times daily. In certain embodiments, treating comprises administering the compound of Formula I, or a pharmaceutically acceptable salt thereof, once daily.

In certain embodiments, treating comprises administering the compound of Formula I, or a pharmaceutically acceptable salt thereof, by a variety of routes including, but not limited to, oral administration, administration as a suppository, topical contact, parenteral administration (e.g., intravenous, intramuscular, intra-arterial, intradermal, subcutaneous, intraperitoneal, intraventricular, and intracranial), intralesional administration, intrathecal administration, intranasal administration, transmucosal administration (e.g., buccal, sublingual, nasal, or transdermal), or the implantation of a slow-release device, e.g., a mini-osmotic pump, to a subject.

In certain embodiments, treating comprises administering the compound of Formula I, or a pharmaceutically acceptable salt thereof, by oral administration.

In certain embodiments, treating comprises administering the compound of Formula I, or a pharmaceutically acceptable salt thereof, as a unit dose.

In certain embodiments, treating comprises administering the compound of Formula I as the free base form.

In certain embodiments, treating comprises administering the compound of Formula I in the form of a pharmaceutically acceptable salt thereof. In some embodiments, the pharmaceutically acceptable salt of the compound of Formula I can be a salt of the compound of Formula I with physiologically compatible mineral acids, such as hydrochloric acid, sulfuric (or sulphuric) acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid.

In certain embodiments, as described above, treating comprises administering the compound of Formula I in a crystalline form (e.g., Form A, Form B, or Form C) in a sulfate salt form (e.g., a monosulfate salt or a hemisulfate salt).

In various embodiments, provided herein are methods of treating medical conditions associated with TSC, comprising administering to a subject in need thereof a composition comprising a therapeutically effective amount of an mGlu5 negative allosteric modulator (NAM), or a pharmaceutically acceptable salt thereof, wherein the mGlu5 NAM is a compound of Formula I:

(I)

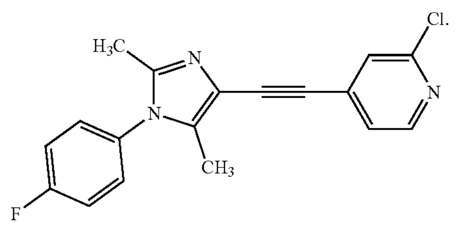

In certain embodiments, treating comprises administering the compound of Formula I as a monotherapy.

In certain embodiments, the methods provided herein further comprise administering a therapeutically effective amount of another therapeutic agent to the subject.

As described above, the present invention relates to use of the compound of Formula I, or a pharmaceutically acceptable salt thereof, for treating a medical condition (e.g., a disease or a disorder) associated with TSC. In certain embodiments, the medical condition associated with TSC is a TSC-associated neuropsychiatric disorder, a TSC-associated tumor, or heart arrhythmia.

In certain embodiments, the medical condition associated with TSC is a TSC-associated neuropsychiatric disorder selected from the group consisting of autism spectrum disorder (ASD), attention deficit hyperactivity disorder (ADHD), anxiety disorder, and depressive disorder.

In certain embodiments, the medical condition associated with TSC is a TSC-associated tumor selected from the group consisting of subependymal giant cell astrocytomas (SEGAs), angiomyolipomas (ALM), renal cell carcinoma, oncocytomas, lymphangioleiomyomatosis (LAM), cardiac rhabdomyomas, ungual fibromas, intraoral fibromas, retinal lesions, retinal hamartomas, and pancreatic neuroendocrine kidney diseases.

In certain embodiments, the medical condition associated with TSC is selected from the group consisting of seizures, intellectual disability, developmental delay, behavioral problems, skin abnormalities, lung diseases, kidney diseases, and heart diseases.

In certain embodiments, the therapeutic effect of the treatment is determined by:

a) reduction of seizure occurrence;
b) reduction of the size of a tumor in the brain, eyes, heart, kidney, skin, or lungs;
c) suppression of tumor growth in the brain, eyes, heart, kidney, skin, or lungs; or
d) improvement of cognitive function.

In some embodiments, the efficacy of the compound is determined by Caregiver Global Impression of Change. In some embodiments, the efficacy of the compound is determined by Sheehan disability scale. In some embodiments, the efficacy of the compound is determined by Patient Self-recorded Seizures.

Without further elaboration, it is believed that one skilled in the art can, based on the above description, utilize the present invention to its fullest extent. The following specific examples are therefore to be construed as merely illustrative, and not limitative of the remainder of the disclosure in any way whatsoever. All publications cited herein are incorporated by reference in their entirety.

EXAMPLES

In order that the disclosure described herein may be more fully understood, the following examples are set forth. The examples described in this application are offered to illustrate the compound, pharmaceutical compositions, and methods described herein and are not to be construed in any way as limiting their scope.

Example 1: Synthesis of 2-chloro-4-[1-(4-fluorophenyl)-2,5-dimethyl-1H-imidazol-4-ylethynyl]pyridine (Compound of Formula I, Supra) [See U.S. Pat. No. 7,332,510]

2-Chloro-4-[1-(4-fluorophenyl)-2-methyl-1H-imidazol-4-ylethynyl]-pyridine (200 mg, 0.6 mmol) was dissolved in 10 mL tetrahydrofuran (THF) and cooled to −75° C. Lithiumdiisopropylamide (0.45 mL, 0.91 mmol) was added and the mixture stirred for 15 min at −75° C. Iodomethane (0.05 mL, 0.85 mmol) was added and stirring was continued at −75° C. for 2 hrs. The reaction mixture was quenched with saturated $NaHCO_3$ solution and extracted with water and ethyl acetate. The combined organic extracts were dried with sodium sulfate, filtered and evaporated. The crude product was purified by flash chromatography on silica gel (heptane/ethyl acetate 90:10 to 20:80 gradient) and by recrystallization from ethyl acetate. The title compound was obtained as a white solid. MS: m/z=326.5 (M+H+).

Example 2: Preparation of Polymorphs of Salts of Compound of Formula I [See U.S. Pat. No. 8,063,076]

Form A monosulfate salt: 61.0 g of 2-chloro-4-[1-(4-fluoro-phenyl)-2,5-dimethyl-1H-imidazol-4-ylethynyl]-pyridine was dissolved in 610 mL of 2-propanol. The solution was filtered and the filter rinsed with 31 mL of 2-propanol. To the combined solutions a mixture of 30 mL of water and 18.91 g of sulfuric acid (97%) was added drop-wise. The solution was cooled to 0-5° C. Seeding was performed at 58° C. as needed. The solid residues were filtered, washed with 2-propanol (0-5° C.) and dried at 50° C. and less than 1 mbar for 18 hrs to provide the monosulfate salt of the compound of Formula I in a yield of 69.1 g (87.1%). Form A seeding crystals can be prepared upon cooling crystallization of a hot solution of 250 mg of the monosulfate salt in 10 mL of 2-propanol. After cooling to 0° C., the solid residues can be filtered and dried at 50° C. under vacuum to afford Form A monosulfate salt, which was confirmed by the XRPD pattern as substantially shown in FIG. 1.

Form B monosulfate salt: 300 mg of Form A monosulfate salt of the compound of Formula I was dissolved in 3 mL 2-propanol and 1 mL water at 60° C. to produce a clear solution. The clear solution was seeded with Form B monosulfate salt and sealed at room temperature (e.g., about 25° C.). Single crystals were formed after 3 days. Seeding crystals can be prepared by formation of a saturated slurry of Form A monosulfate salt of the compound of Formula I in 2-propanol and water (3:1 v/v) at room temperature. The slurry was stirred at room temperature for approximately 3 weeks. The solids were filtered via a glass 35 filter to afford crystalline Form B monosulfate salt, which was confirmed by the XRPD pattern as substantially shown in FIG. 2.

Form C hemisulfate salt: 41 g of Form A monosulfate of the compound of Formula I was mixed with 128 g of water. The slurry was stirred at room temperature for 2-16 hrs. After all the Form A monosulfate salt had been converted to the hemisulfate salt, the resulting crystals were collected by filtration and rinsed with water. The wet cake thus obtained was dried at 40° C. in a vacuum oven for 48 hrs to afford Form C hemisulfate salt in a yield of 93%. Form C hemisulfate salt was confirmed by the XRPD pattern as substantially shown in FIG. 3.

Amorphous monosulfate salt: 0.53 g of a monosulfate of the compound of Formula I was dissolved in 10 mL of methanol at approximately 65° C. After complete evaporation of the solvent under vacuum, the solid (foam) was further dried at about 50° C. under 5-20 mbar for 18 hrs. Analysis (XRPD and DSC) revealed amorphous form of the compound of Formula I was obtained. The amorphous monosulfate salt was characterized by an infrared spectrum having bands at 2730, 2592, 2219, 1633, 1586, 1570, 1513, 1375, 1343, 1293, 1226, 1157, 1130, 1084, 1040, 986, 903, 848, 788, 712 and 670 $cm^{-1}$ (±3 $cm^{-1}$). The glass transition temperature ($T_g$) of the amorphous form determined by DSC was largely dependent on the solvent content and was observed for the wet sample (closed pan) at about 42° C. and for the in-situ dried sample (pan with perforation lid) at about 77° C.

Example 3: Modified Release Matrix Pellet Capsules of Form A Monosulfate Salt Two different matrix pellet compositions were prepared according to the formulations shown in Table 1 below. The matrix pellets thus obtained were filled into capsules to afford matrix pellet capsules. The process included: high shear wet granulating Form A monosulfate salt, microcrystalline cellulose, methacrylic acid copolymer, and hypromellose, with purified water to form a mixture; followed by extruding, spheronizing, fluid bed drying, and sieving the mixture to provide a solid material; and subsequently blending the solid material with an external pharmaceutical excipient, talc, to afford matrix pellets; and then filling the matrix pellets into capsules to provide matrix pellet capsules. More specifically, each of the granulating, extruding, spheronizing, drying, sieving, and blending steps was carried out as follows.

1. Weighed the Form A monosulfate and about 15% of the required amount of microcrystalline cellulose and place them into a suitable container. Mixed the contents using a turbula mixer or an equivalent blender for 30 minutes at 40±10 rpm.
2. Weighed all the other excipients: methacrylic acid copolymer, hypromellose, and the remaining microcrystalline cellulose.
3. Transferred all the materials from Step 2 into a high shear granulator followed by the mixture from Step 1. Mix all the components for two minutes using the impeller and chopper at the following speeds: Impeller: 300±100 rpm and Chopper: 1500±500 rpm.
4. Granulated the powder mixture from Step 3 by spraying purified water (approximately 83% of the batch size) onto the powder mixture in the high shear granulator while continually mixing the contents using the impeller at 300±100 rpm and Chopper at 1500±500 rpm for 20 minutes. Recorded the power consumption at the granulation end point.
5. Fed the wet granules at a uniform rate and extruded the wet granules through the extruder using screen #1.0 mm and speed setting of about 40±5 rpm.
6. Transferred about 700 g of the extruded material from Step 5 into a spheronizer using #1 graded plate. Spheronized the contents for 5±1 minutes at a speed of about 0.6 (approximately 1000 rpm).
7. Collected the spheronized material from Step 6 and dried in a fluid bed dryer with inlet temperature of 60±10° C., until the water content of the pellets was less than 0.8% measured using a Halogen Moisture Analyzer or an equivalent set at 90° C.
8. Screened the dried pellets from Step 7 through size #10 and #40 screens and collected the pellet fraction between #10 and #40 screen.
9. Used the weight of the pellets from Step 8 to weigh the adjusted amount of talc.
10. Placed the pellets from Step 9 in a bin blender or an equivalent, added talc and mixed for 5 minutes at 20±5 rpm.
11. Filled the pellets from Step 10 into hard gelatin capsules.
12. Stored the filled capsules from Step 11 in double polyethylene-lined bags with two silica gel bags between the polyethylene bags in a closed fiber drum at a temperature not above 25° C.

TABLE 1

Matrix Pellet Formulations

| Ingredient | Quantity (mg/capsule) | | Function |
|---|---|---|---|
| Form A monosulfate | 0.13* | 1.30# | Active ingredient |
| Microcrystalline cellulose | 64.62 | 128.20 | Matrix forming polymer |
| Methacrylic acid copolymer | 30.00 | 60.00 | pH-responding polymer |
| Hypromellose | 5.00 | 10.00 | Binder |
| Talc | 0.25 | 0.50 | Glidant |
| Total | 100.00 | 200.00 | |

*Represents 0.1 mg dosage and #represents 1.0 mg dosage described in the paragraph below.

The content uniformity of the matrix pellets was found to be dependent on the median particle size (Dv50) and amount of the Form A monosulfate salt ("API"). Specifically, three API variants achieved by size reduction with jet mill and pin mill to a respective median particle size (Dv50) of 3.3 μm (jet-milled), 10 μm (pin-milled), and 47 μm (pin-milled) were manufactured at two different dosages (API: 0.1 mg and 1.0 mg). At the dosage of 1.0 mg of API, matrix pellets prepared using API with Dv50 of 3.3 μm, 10 μm, and 47 μm exhibited USP uniformity of dosage units (UDU) acceptance value (AV) of 2.2, 6.3, 3.4, respectively, all meeting the UDU acceptance criteria (AV<15). At the dosage of 0.1 mg of API, matrix pellets prepared using API with Dv50 of 47 μm failed to meet the UDU acceptance criteria with an AV of 20.9; unexpectedly, matrix pellets prepared using API with Dv50 of 3.3 μm and 10 μm met the UDU acceptance criteria with an AV of 6.0 and 10.3, respectively. API particle size (Dv50) of 10 μm or less (e.g., between 3.3-10 μm) was shown to provide matrix pellets drug product with acceptable manufacturing process and drug product performance (e.g., content uniformity, pellet size distribution, and dissolution), thus more suitable for pharmaceutical drug development.

Example 4: A Study of the Compound of Formula I for Treatment of Subjects With Tuberous Sclerosis Complex (TSC)

A Phase 2B, multicenter, 30-week, prospective, crossover, double-blind randomized, placebo-controlled study is carried out, as shown in Table 2 and description below, to evaluate the efficacy and safety of daily 1.0 mg to 3.0 mg or 1.5 mg to 3.5 mg of the compound of Formula I ("CF-I")

adjunctive to ongoing epilepsy therapy in 55 patients with TSC who received a suboptimal response to their current anti-seizure therapy. Specifically, the study is done on patients with TSC who, despite optimal treatment with antiseizure therapies, show persistence of at least one type of focal or generalized seizure, including absences, drop seizures (atonic, tonic, tonic-clonic or myoclonic) for at least six months prior to study entry.

Basimglurant dosing follows two weight categories (<40 kg and ≥40 kg). The initial dose of basimglurant is 1.0 mg once daily for patients weighing <40 kg, and 1.5 mg once daily for patients weighing ≥40 kg. The maximum doses of basimglurant are 3.0 mg once daily for patients <40 kg, and 3.5 mg once daily for patients ≥40 kg. Thereafter, the dose of basimglurant is escalated in a blinded fashion in 0.5 mg increments at weekly intervals according to individual tolerability. Once the dose escalation phase is completed, patients continue to receive the same dose of basimglurant throughout the maintenance phase.

TABLE 2

Study Protocol - objectives and endpoints

| Objectives | Endpoints |
|---|---|
| **Primary** | |
| To evaluate the efficacy of a double-blind, daily basimglurant administration, adjunctive to standard of care seizure therapy compared with placebo adjunctive to standard of care seizure therapy in patients with Tuberous Sclerosis Complex (TSC). | Mean percentage change from baseline of seizure frequency during the maintenance dosing in Period 2 (Weeks 13 to 16) and Period 4 (Weeks 27-30). |
| **Secondary** | |
| To evaluate the number of patients considered treatment responders. | Number of patients showing a ≥25% reduction in seizures from baseline at the end of each 4-week maintenance period (Periods 2 and 4).<br>Number of patients showing a ≥50% reduction in seizures from baseline at the end of each 4-week maintenance period (Periods 2 and 4).<br>Number of patients showing a ≥75% reduction in seizures from baseline at the end of each 4-week maintenance period (Periods 2 and 4).<br>Number of patients showing a ≥100% reduction in seizures from baseline at the end of each 4-week maintenance period (Periods 2 and 4). |
| To determine the longest seizure free interval (i.e., seizure free days). | Number of seizure free days per maintenance dosing during Period 2 (Weeks 13 to 16) and Period 4 (Weeks 27-30). |
| To determine the effect of basimglurant on the severity of symptoms of TSC. | Changes in Caregiver Global Impression of Change (CGIC) score during the maintenance dosing in Period 2 (Weeks 13 to 16) and Period 4 (Weeks 27-30). |
| To evaluate the impact of treatment on functioning on school and social activities. | Changes in Sheehan Disability Scale in the maintenance dosing during Period 2 (Weeks 13 to 16) and Period 4 (Weeks 27-30). |
| To evaluate the safety of basimglurant in children and adolescents with seizures associated with TSC. | Safety and tolerability will be evaluated in terms of incidence, nature, and severity of adverse events, vital signs, physical examination, clinical chemistry, hematology, electrocardiograms, and urinalysis, as well as treatment delays, dose reductions, and dose discontinuations. In addition, suicidal ideation will be assessed using S-STS. |
| To investigate the proportion of patients tolerating each dose during dose escalation. | Proportion of patients with the 95% confidence intervals of patients reaching each dose level during the dose escalation in Periods 2 and 4.<br>Proportion of patients with the 95% confidence intervals of patients tolerating each dose level during the dose escalation in Periods 2 and 4. |

Recruitment is initiated in patients aged 12-18 years. After at least 8 patients have completed Period 2, the data and safety monitoring board (DSMB) reviews the safety data. Based on the outcome of this review, the remaining group of patients, aged 5-11 years, is randomized to treatment.

Part A

Part A comprises 4 periods. Period 1 is stabilization period (baseline) is 4 weeks. During this period, patients receive placebo and patients are monitored to ensure stability of their previous antiepileptic medications and to accurately record the frequency and duration of their seizures. Period 2 is 12 weeks double-blind treatment (study weeks 5 to 16). During this period, patients are randomized to basimglurant or placebo. Period 3 is 2 weeks washout (study weeks 17 and 18) of basimglurant, patients receive placebo. Period 4 is 12 weeks double-blind treatment (study weeks 19 to 30). During this period, patients who initially received placebo are assigned to receive basimglurant, and those who initially received basimglurant receive placebo.

Basimglurant or matching placebo is administered once daily (preferably in the morning) with food for 12 weeks in Periods 2 and 4 (Weeks 5-16 and 19-30, respectively). In each of these two periods, an initial 5-week dose escalation phase is followed by a 7-week maintenance phase. At each dose increment step the investigator makes an overall assessment of the safety and tolerability of the current dose. Dose escalation only happen if the current dose is considered adequately tolerated, and the patient and their caregiver are in agreement. In the event of inadequate tolerability, patients can either continue on same dose or de-escalate by 0.5 mg at the discretion of the investigator.

Patients receiving placebo undergoes sham dose escalation based on the same decision criteria in order to maintain blinding. On study day 211, patients who complete Periods 1-4 of the study and have tolerated the study medication are offered to participate in a 52-week OLE study (Part B).

Part B

Part B comprises a 52-week OLE where all patients receives basimglurant. All OLE study participants restarts on basimglurant at the lowest dose according to their body weight, which are titrated to the maximum individually tolerated dose and are maintained on that dose until study end.

Seizure frequency during study Periods 1-4 and the 52-week OLE period are monitored and recorded using patient/carer diaries and, if available at the time of study start, a wearable device that detects and records possible focal and generalized tonic-clonic seizures.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method of preparing a matrix pellet composition comprising a crystalline anhydrate form (Form A) of a monosulfate salt of a compound of Formula I:

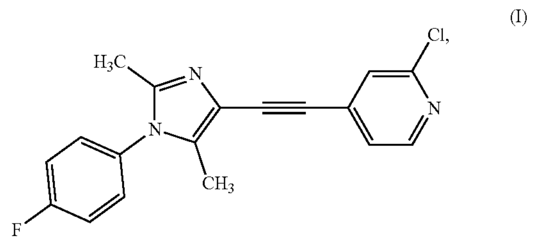 [SMILES: Cc1nc(C#Cc2ccnc(Cl)c2)c(C)n1-c1ccc(F)cc1]

(I)

the method comprising:

granulating the Form A monosulfate salt and one or more polymers with purified water to form a mixture;

extruding, spheronizing, drying, and sieving the mixture to afford a solid material; and blending the solid material with another pharmaceutical excipient to afford a matrix pellet, wherein the Form A monosulfate salt is characterized by at least three peaks selected from the following X-ray powder diffraction peaks obtained with a $Cu_{K\alpha}$ radiation at 2θ (2 Theta): 9.8±0.2°, 13.4±0.2°, 14.2±0.2°, 18.1±0.2°, 18.9±0.2°, 19.6±0.2°, 22.6±0.2°, 22.9±0.2°, 25.7±0.2°, 27.1±0.2°, and 29.9±0.2°, and has a particle size (Dv50) of about 3.3 μm to about 10 μm.

2. The method of claim 1, wherein the one or more polymers are selected from the group consisting of a cellulose, methacrylic acid copolymer, and hypromellose.

3. The method of claim 1, wherein the other pharmaceutical excipient comprises talc.

4. The method of claim 1, wherein the matrix pellet composition is a modified release matrix pellet composition.

5. The method of claim 1, wherein the Form A monosulfate salt is characterized by the following XRPD peaks obtained with a $Cu_{K\alpha}$ radiation at 2θ (2 Theta): 9.8±0.2°, 13.4±0.2°, 14.2±0.2°, 18.1±0.2°, 18.9±0.2°, 19.6±0.2°, 22.6±0.2°, 22.9±0.2°, 25.7±0.2°, 27.1±0.2°, and 29.9±0.2°.

6. The method of claim 1, wherein the Form A monosulfate salt is present in the matrix pellet composition in an amount from about 0.05 mg to about 20 mg.

7. The method of claim 1, wherein the Form A monosulfate salt is present in the matrix pellet composition in an amount from about 0.5 mg to about 4.0 mg.

8. The method of claim 1, wherein the Form A monosulfate salt is present in the matrix pellet composition in an amount of about 0.65 mg.

9. The method of claim 1, wherein the Form A monosulfate salt is present in the matrix pellet composition in an amount of about 1.3 mg.

10. The method of claim 1, wherein the Form A monosulfate salt is present in the matrix pellet composition in an amount from about 0.01% to about 20% by weight, based on the total weight of the matrix pellet composition.

11. The method of claim 1, wherein the Form A monosulfate salt is present in the matrix pellet composition in an amount from about 0.1% to about 2% by weight, based on the total weight of the matrix pellet composition.

12. The method of claim 1, wherein the Form A monosulfate salt is present in the matrix pellet composition in an amount of about 0.13% by weight, based on the total weight of the matrix pellet composition.

13. The method of claim 1, wherein the Form A monosulfate salt is present in the matrix pellet composition in an amount of about 1.3% by weight, based on the total weight of the matrix pellet composition.

* * * * *